United States Patent [19]

Sell

[11] Patent Number: 4,579,680
[45] Date of Patent: Apr. 1, 1986

[54] ALIPHATIC NITRILES

[75] Inventor: Charles S. Sell, Kent, England

[73] Assignee: Internationale Octrooi Maatschappij "Octropa" B.V., Rotterdam, Netherlands

[21] Appl. No.: 671,015

[22] Filed: Nov. 13, 1984

Related U.S. Application Data

[63] Continuation of Ser. No. 413,446, Aug. 31, 1982, abandoned.

[30] Foreign Application Priority Data

Sep. 3, 1981 [GB] United Kingdom ............... 8126748

[51] Int. Cl.$^4$ .......................... A61K 7/46; C11B 9/00; C11D 3/50
[52] U.S. Cl. ................. 252/522 R; 252/106; 252/174.11; 424/69; 424/70; 424/71; 558/435
[58] Field of Search ................. 252/522 R; 260/465.1

[56] References Cited

U.S. PATENT DOCUMENTS

| | | | |
|---|---|---|---|
| Re. 27,332 | 4/1972 | Somerville et al. | 252/522 R |
| 2,912,455 | 11/1959 | Smiley | 260/465.8 R |
| 3,531,510 | 9/1970 | Blumenthal | 252/522 R X |
| 3,739,007 | 6/1973 | Schwager et al. | 260/464 |
| 3,899,398 | 8/1975 | Cole et al. | 203/49 |
| 4,193,934 | 3/1980 | Bauer et al. | 252/522 R X |
| 4,277,377 | 7/1981 | Webb et al. | 252/522 R |

OTHER PUBLICATIONS

Fischli, Helvetica Chimica Acta., vol. 61, (1978), pp. 2560-2578.
Arctander, Perfume and Flavor Chemicals, (1969) vol. 1, Compound 1121; vol. 2, Compounds 2130, 2292, 2362 and 3010.
Beilsteins Handbuch der Organischen Chemie; vol. 2, 1942, second supplement; pp. 312, 315, 316, 323.
Beilsteins Handbuch der Organischen Chemie; vol. 2, 1960, third supplement; pp. 825, 826, 831, 832, 848, 853, 863, 864, 865, 979.
Croteau (editor); "Fragrance and Flavor Substances", (1980), pp. 123-128, article by Hagena et al.; D&PS. Verlag, 3017 Pattersen 1, W. Germany.
De Simone, "Perfumer & Flavorist," vol. 4, (1980), pp. 2, 3, 4, 6, 7 and 8.
Sell, et al: Perfumer & Flavorist, 7 (1983), 14-16.

Primary Examiner—Joseph Paul Brust
Attorney, Agent, or Firm—Cushman, Darby & Cushman

[57] ABSTRACT

This invention provides perfume compositions containing certain substituted saturated aliphatic nitriles and some novel nitriles useful as perfumery components.

1 Claim, No Drawings

ALIPHATIC NITRILES

This is a continuation of application Ser. No. 413,446, filed Aug. 31, 1982, now abandoned.

This invention relates to substituted saturated aliphatic nitriles, more particularly to alpha- and beta-substituted nitriles which have been found to have value in perfume compositions.

Various substituted aliphatic nitriles have been known for some years, but hitherto their value as perfume components has not been appreciated. Our work has shown that certain of the alpha- and beta-substituted aliphatic nitriles, some of which are novel, have particular merit in perfumery compositions.

Accordingly, the present invention provides a perfume composition comprising perfume components and an organoleptically discernible amount of a nitrile of the formula:

$$CH_3(CH_2)_nRCN$$

in which
R=—CHCH$_3$— or —CHCH$_3$CH$_2$— and in which, when
R=—CHCH$_3$—, n is an integer from 5–9 and when
R=—CHCH$_3$CH$_2$—, n is an integer from 4–8.

In addition, this invention provides certain novel substituted nitriles of particular value in perfume formulations, having the formula:

$$CH_3(CH_2)_nCHCH_3CH_2CN$$

in which n is 6, 7 or 8.

The nitriles useful in perfume compositions provided by this invention have, in addition to their useful odour characteristics, good stability when used in perfume formulations which are to be used or stored in an aggressive environment, such as in soaps, disinfectants, laundry powders and other compositions in which active chemicals are present or which have to withstand the effects of daylight or heat.

The nitriles useful according to this invention may be prepared by various processes, but a convenient process for the preparation of the alpha-substituted nitriles is as follows:

Procedure A

A solution of the required methyl alkyl ketone (50 m mol) and tosylmethylisocyanide (12 g, 60 m mol) in dry diglyme (120 ml) was added over 15 minutes at 0° C. under nitrogen to a stirred solution of potassium t-butoxide (freshly prepared from potassium 4.3 g, 0.11 g atom) in dry t-butanol (100 ml) and diglyme (100 ml). When the addition was complete, the mixture was allowed to warm to room temperature then stirred for 2 hours and left to stand overnight. The resultant solution was poured into water (400 ml) and extracted with light petroleum (3×100 ml, bp 40°–60° C.). The combined organic extracts were washed with water (2×500 ml), then brine (500 ml) and dried (MgSO$_4$). The solvent was removed under reduced pressure and the residue chromatographed using a column (3 cm diameter, 30 cm height) of silica gel with 5% ether in light petroleum (bp 40°–60° C.) as solvent. Those fractions containing the product were freed of solvent under reduced pressure and the residue distilled to give the desired 2-methyl substituted nitrile.

A convenient process for the preparation of the betanitriles is as follows:

Procedure B

The required methyl alkyl ketone (1 mol), cyanoacetic acid (93.5 g, 1.1 mol), ammonium acetate (13 g, 0.17 mol) and toluene (175 ml) were stirred under reflux (pot temperature 140°–160° C.) in a Dean-Stark apparatus until carbon dioxide ceased to be evolved (3–6 hours). The resultant mixture was cooled, washed with saturated aqueous sodium hydrogen carbonate (2×50 ml) and water (50 ml) then the solvent was removed under reduced pressure. The crude mixture of nitriles was then added to one quarter of its volume of 50% aqueous sodium hydroxide to which Tergitol* (3 drops) had been added. The resulting mixture was stirred under reflux for 1 hour then cooled. The organic layer was removed, washed with water (3×50 ml) and distilled. 5% Palladium on carbon (0.1% by weight relative to the nitrile mixture) was then added followed by ethyl acetate (2×weight of distillate) and the suspension stirred vigorously in an atmosphere of hydrogen until uptake of gas ceased. The catalyst was removed by filtration and the solvent by evaporation under reduced pressure. Fractional distillation of the residue afforded the desired 3-methyl substituted nitrile.

*Tergitol is a trade name for a surfactant (Union Carbide).

The following table sets out the physical and the organoleptic properties of the nitriles useful in this invention:

TABLE

| Sample | Series | Carbon Chain Length | Name | Structure |
|---|---|---|---|---|
| 1 | α-methyl | 8 | 2-methyloctanonitrile | CH$_3$(CH$_2$)$_5$CHCH$_3$CH |
| 2 | α-methyl | 9 | 2-methylnonanonitrile | CH$_3$(CH$_2$)$_6$CHCH$_3$CN |
| 3 | α-methyl | 10 | 2-methyldecanonitrile | CH$_3$(CH$_2$)$_7$CHCH$_3$CN |
| 4 | α-methyl | 11 | 2-methylundecanonitrile | CH$_3$(CH$_2$)$_8$CHCH$_3$CN |
| 5 | α-methyl | 12 | 2-methyldodecanonitrile | CH$_3$(CH$_2$)$_9$CHCH$_3$CN |
| 6 | β-methyl | 8 | 3-methyloctanonitrile | CH$_3$(CH$_2$)$_4$CHCH$_3$CH$_2$CN |
| 7 | β-methyl | 9 | 3-methylnonanonitrile | CH$_3$(CH$_2$)$_5$CHCH$_3$CH$_2$CN |
| 8 | β-methyl | 10 | 3-methyldecanonitrile | CH$_3$(CH$_2$)$_6$CHCH$_3$CH$_2$CN |
| 9 | β-methyl | 11 | 3-methylundecanonitrile | CH$_3$(CH$_2$)$_7$CHCH$_3$CH$_2$CN |
| 10 | β-methyl | 12 | 3-methyldodecanonitrile | CH$_3$(CH$_2$)$_8$CHCH$_3$CH$_2$CN |

| Sample | Preparation | Boiling Point (lit. bp) | Odour Description |
|---|---|---|---|
| 1 | Procedure A, 76% yield from 2-octanone | 78–80° C. at 8 m bar (85 at 10 mm Hg) | Floral jasminic character with some celery aspects and a hint of coconut/lactone - very diffusive. |
| 2 | Procedure A, 69% yield | 72–73° C. at 3 m bar | Soft, floral, lactonic, |

TABLE-continued

| | | | |
|---|---|---|---|
| | from 2-nonanone | (100 at 10 mm Hg) | jasmine/peachy character. |
| 3 | Procedure A, 77% yield from 2-decanone | 85–87° C. at 3 m bar (115 at 10 mm Hg) | A fine, light, jasmine/floral character with a soft peach quality. |
| 4 | Procedure A, 74% yield from 2-undecanone | 84° C. at 1 m bar (133 at 12 mm Hg) | Fresh, floral with some lilac character - tenacious. |
| 5 | Procedure A, 59% yield from 2-dodecanone | 125–127° C. at 7 m bar (146 at 10 mm Hg) | Soft, floral with a green jasminic type odour - very persistent. |
| 6 | Procedure B, 59% yield from 2-heptanone | 66–68° C. at 4 m bar (207–8 at 760 mm Hg) | An unusual floral type consisting of a distinct fatty jasminic character combined with an agrumen quality. |
| 7 | Procedure B, 16% yield from 2-octanone | 93° C. at 8 m bar (95–6 at 2–3 mm Hg) | Fresh, jasminic floral type with a slightly green quality. |
| 8 | Procedure B, 49% yield from 2-nonanone | 72–74° C. at 0.7 m bar | Soft, citrus floral - reminiscent of jasmine. |
| 9 | Procedure B, 35% yield from 2-decanone | 99–100° C. at 3 m bar | Light, fresh, green, floral suggesting lilac, with slight citrus undertones. |
| 10 | Procedure B, 26% yield from 2-undecanone | 95–97° C. at 0.7 m bar | Distinct orange character which is suffused by a light green sea-fresh quality. |

The following are two examples of perfume compositions comprising the nitriles of this invention:

Formula 1

| | |
|---|---|
| Phenylethyl Alcohol | 30.5 |
| Terpineol | 6.0 |
| Paratertiary butyl cyclohexyl acetate high cis (PPL) | 15.0 |
| Benzyl Salicylate | 14.8 |
| Cinnamic Alcohol | 10.0 |
| Sandalone (PPL) | 5.0 |
| Galaxolide (IFF) | 3.0 |
| Hexyl Cinnamic Aldehyde | 10.0 |
| Coumarin | 2.0 |
| Rose Base AB 380 (PPL) | 2.0 |
| Isoeugenol | 0.1 |
| Vetivert Brazilian | 0.1 |
| Nitrile No 3 | 1.5 |

Formula 1 in the absence of nitrile 3 has a floral, woody bouquet suitable for a toilet soap. The addition of 1.5% of nitrile 3 enhances the overall freshness, giving a light floral, fruity effect. Using the above formulation but substituting nitrile 9 in place of nitrile 3, a perfume is created having an added fresh lightness with an enhanced floral, fruity and citrus character.

The three novel nitriles provided by this invention are those numbered 8, 9 and 10 in the samples list and their mass spectral data are as follows.

| Sample | Base Peak | M1 | M2 | M3 | M4 | M5 |
|---|---|---|---|---|---|---|
| 8 | $C_{10}$ | 41 | 43:85 | 57:84 | 68:66 | 55:50 | 96:46 |
| 9 | $C_{11}$ | 41 | 57:85 | 43:84 | 68:56 | 55:50 | 69:43 |
| 10 | $C_{12}$ | 41 | 57:92 | 43:90 | 55:54 | 68:53 | 70:48 |

Perfumes formulated using as an odorous component the nitriles provided by this invention may be employed in the various products, such as soaps, detergents, hairsprays, talcum powders and the like, which are normally augmented by the addition of a perfume.

I claim:

1. A perfume composition comprising at least two perfume components and, in addition, as an odour providing component, an organoleptically discernible amount of a nitrile of the formula:

$$CH_3(CH_2)_nRCN$$

in which
R = —CHCH$_3$— or —CHCH$_3$CH$_2$— and in which, when
R = —CHCH$_3$—, n is an integer from 5–9 and when
R = —CHCH$_3$CH$_2$—, n is an integer from 4–8,
the amount of the nitrile not exceeding 95% by weight of the perfume composition and the nitrile being characterized by its stability in the use or storage of said composition.

* * * * *